United States Patent [19]
Fallik

[11] Patent Number: 5,922,013
[45] Date of Patent: Jul. 13, 1999

[54] MICROWAVE BODY HEATING SYSTEM

[76] Inventor: Joel Fallik, 56 Arthur Pl., Yonkers, N.Y. 10701

[21] Appl. No.: 08/645,188

[22] Filed: May 13, 1996

Related U.S. Application Data

[63] Continuation of application No. 08/252,422, Jun. 1, 1994, abandoned.

[51] Int. Cl.$^6$ ..................................................... A61N 5/00
[52] U.S. Cl. .............................. 607/101; 607/154; 606/33
[58] Field of Search .............................. 607/96–102, 103, 607/154–156; 600/430; 606/33

[56] References Cited

U.S. PATENT DOCUMENTS

| | | | |
|---|---|---|---|
| 4,190,053 | 2/1980 | Sterzer | 607/96 |
| 4,316,474 | 2/1982 | Spethmann | 607/156 |
| 4,632,127 | 12/1986 | Sterzer | 607/156 |
| 4,641,659 | 2/1987 | Sepponen | 128/653 |
| 4,672,980 | 6/1987 | Turner | 607/154 |
| 4,774,961 | 10/1988 | Carr | 128/736 |
| 4,866,231 | 9/1989 | Schneider | 607/101 |
| 4,974,587 | 12/1990 | Turner et al. | |
| 5,010,897 | 4/1991 | Leveen | 607/101 |
| 5,097,844 | 3/1992 | Turner | |
| 5,148,814 | 9/1992 | Kikuchi et al. | 607/101 |
| 5,441,532 | 8/1995 | Fenn | 607/101 |
| 5,501,655 | 3/1996 | Rolt et al. | 607/154 |
| 5,571,154 | 11/1996 | Ren | 607/156 |

FOREIGN PATENT DOCUMENTS

| | | | |
|---|---|---|---|
| 0293080 A2 | 11/1988 | European Pat. Off. | 607/154 |
| 0334274 A2 | 9/1989 | European Pat. Off. | 607/154 |
| 0336370 | 10/1989 | European Pat. Off. | 607/154 |
| 0370597 A2 | 5/1990 | European Pat. Off. | 607/154 |
| 0519415 | 12/1992 | European Pat. Off. | 607/101 |
| 2354403 | 5/1975 | Germany | 607/101 |
| 1522503 | 2/1992 | U.S.S.R. | 607/101 |

OTHER PUBLICATIONS

Herrick; "Application of Microwaves in Physical Medicine"; 1952 IRE NAT'L Convention; pp. 76–1–3 and 1–9.

W. H. Newman et al., "Tumor Perfusion During Microwave Hyperthermia: Preliminary Measurements," Proceedings of Eighth Annual Conference of the IEEE/Engineering in Medicine and Biology Society, IEEE Cat. No. 86CH2368–9, pp. 1503–1506 (1986).

P.R. Stauffer et al., "Comparative Thermal Dosimetry of Interstitial Hyperthermia," Proceedings of Eighth Annual Conference of the IEEE/Engineering in Medicine and Biology Society, IEEE Cat. No. 86CH2368–9, pp. 1458–1462 (1986).

(List continued on next page.)

*Primary Examiner*—Danton D. DeMille
*Assistant Examiner*—David M. Ruddy
*Attorney, Agent, or Firm*—Baker & Botts, LLP

[57] ABSTRACT

A microwave body heating system uses one or more focused beams of microwave energy. A fan beam or transversely scanned beam is directed to a narrow transverse section of a subject's body. The transversely scanned or fan beam is moved longitudinally down the body in a controlled sequential incremental manner. Scanning times, patterns and radiated power levels are controlled in experimentally predetermined or monitored formats to achieve desired levels of heating of an entire body or localized area. Microwave frequency energy is provided by one or more magnetron type devices in a variably positionable microwave power assembly which is longitudinally scanned under control of a motor device.

15 Claims, 2 Drawing Sheets

OTHER PUBLICATIONS

J.W. Strohbehn, "Use of Heat in Cancer Therapy," Proceedings of a Special Symposium on Critical Emerging Issues in Biomedical Engineering, IEEE Cat. No. 86CH2369–7, pp. 76–78 (1986).

A.H. Wilson et al., "Control of the Power Deposition Pattern of an Interstitial Microwave Antenna Hyperthermia System," Proceedings of the Twelfth Annual Northeast Bioengineering Conference, IEEE Cat. No. 86CH2329–1, pp. 205–208 (1986).

K.M. Jones et al., "SAR Patterns from an Interstitial Microwave Antenna Array Hyperthermia System," Proceedings of the Twelfth Annual Northeast Bioengineering Conference, IEEE Cat. No. 86CH2329–1, pp. 209–212 (1986).

Robert W. Paglione et al., "Instrumentation for Invasive and Non–Invasive Microwave Hyperthermia of Brain Tumors," 1986 IEEE–MTT–S International Microwave Symposium Digest, IEEE Cat. No. 86CH2301–0, pp. 767–769 (1986).

MICROWAVE BODY HEATING SYSTEM

This application is a continuation of application Ser. No. 08/252,422, filed on Jun. 1, 1994, now abandoned.

This invention relates to systems enabling the controlled application of radiated microwave energy to achieve warming of a subject body portion and, more particularly, to the heating of the entire body of a subject on an incremental sequential scanning basis.

BACKGROUND OF THE INVENTION

In various situations it may become desirable to warm or heat a body portion of a subject on a relatively rapid, but controlled basis, in order to achieve a predetermined level of warming. While various methods and approaches have been available for such purposes, they have tended to be slow, ineffective or not readily controllable as to the degree of warming or heating achieved. It has also been difficult to control the positional application and effects to selected areas, relative to other body portions. Certain other mediums, such as x-rays, are difficult to contain and potentially injurious to equipment operators. Also, many potential approaches and mediums capable of providing body heating are not amenable to heating of a subject's entire or substantially entire body on a readily controllable basis.

It is therefore an object of the present invention to provide new and improved systems and methods for heating body portions, and such systems utilizing controlled application of microwave energy, which may be applied on an incremental sequential basis under computer control.

SUMMARY OF THE INVENTION

In accordance with the invention, a system, to heat body portions using controlled microwave energy, includes a support unit arranged to support a subject body portion and having transverse and longitudinal dimensions. A microwave power assembly is arranged to be variably positionable relative to the support unit and to radiate at least one focused directional beam of microwave frequency energy at a controllable power level to irradiate a section transverse to the support unit. A position adjustment element is arranged to controllably relatively position the microwave power assembly and the support unit longitudinally. The system also includes a central processor unit coupled to the position adjustment element, arranged to control longitudinal positioning of the microwave power assembly and also arranged to control at least one of the following: the power level, the beam focus and the beam direction of a beam of microwave frequency energy radiated by the microwave power assembly.

Also in accordance with the invention, a method, to heat body portions using controlled microwave energy, comprises the steps of:
 (a) positioning a subject body portion on a support unit having transverse and longitudinal dimensions;
 (b) irradiating a section transverse to the support unit by a focused directional beam of microwave frequency energy at a controllable power level radiated by a variably positionable microwave power assembly;
 (c) controllably relatively positioning the microwave power assembly and the support unit longitudinally; and
 (d) controlling at least one of the power level, the beam focus and the beam direction of the beam of microwave frequency energy radiated by the microwave power assembly.

For a better understanding of the invention, together with other and further objects, reference is made to the accompanying drawings and the scope of the invention will be pointed out in the accompanying claims.

DESCRIPTION ON THE INVENTION

Figure 1:
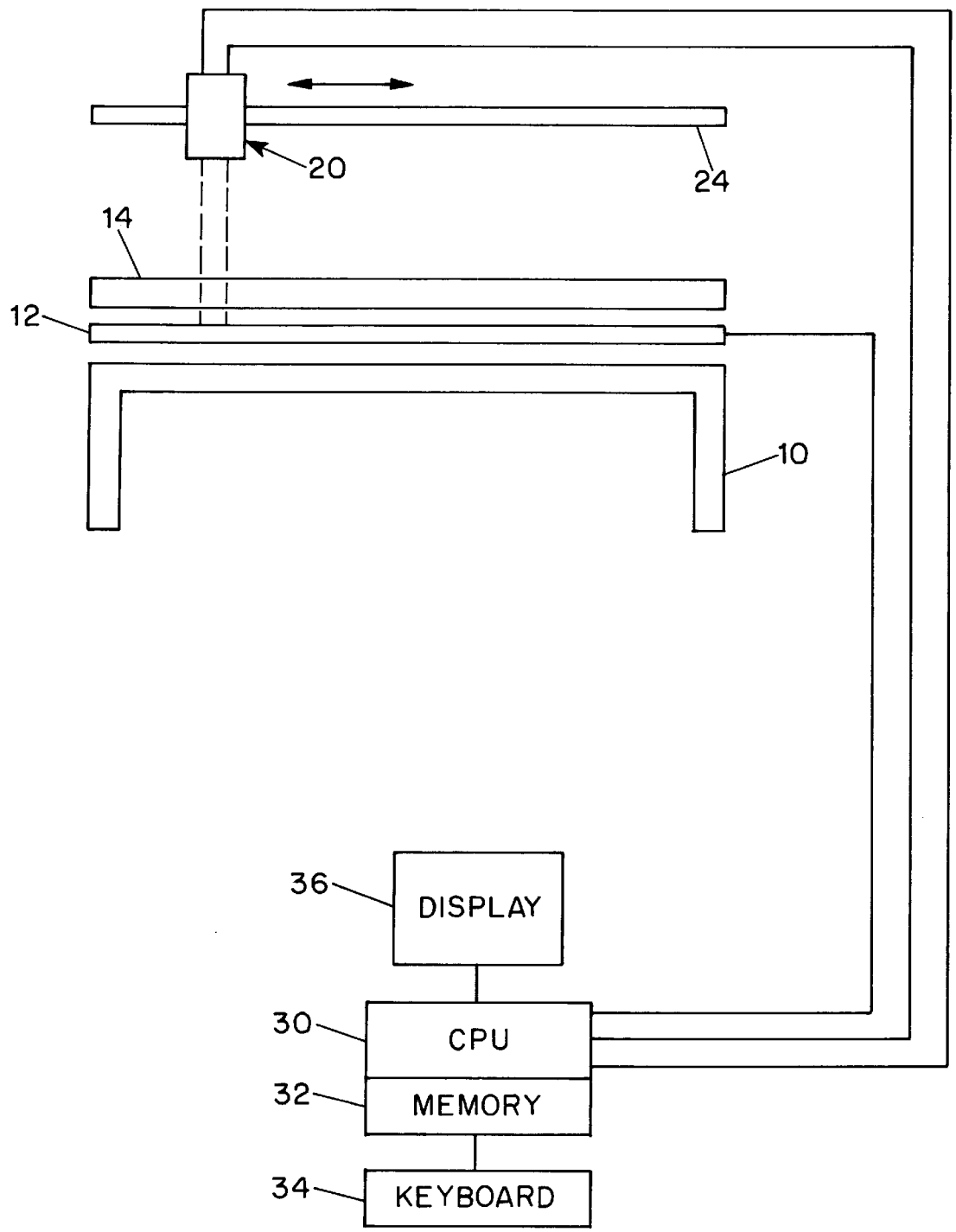
FIG. 1 illustrates, in side view, an embodiment of a system in accordance with the invention.
Figure 2:
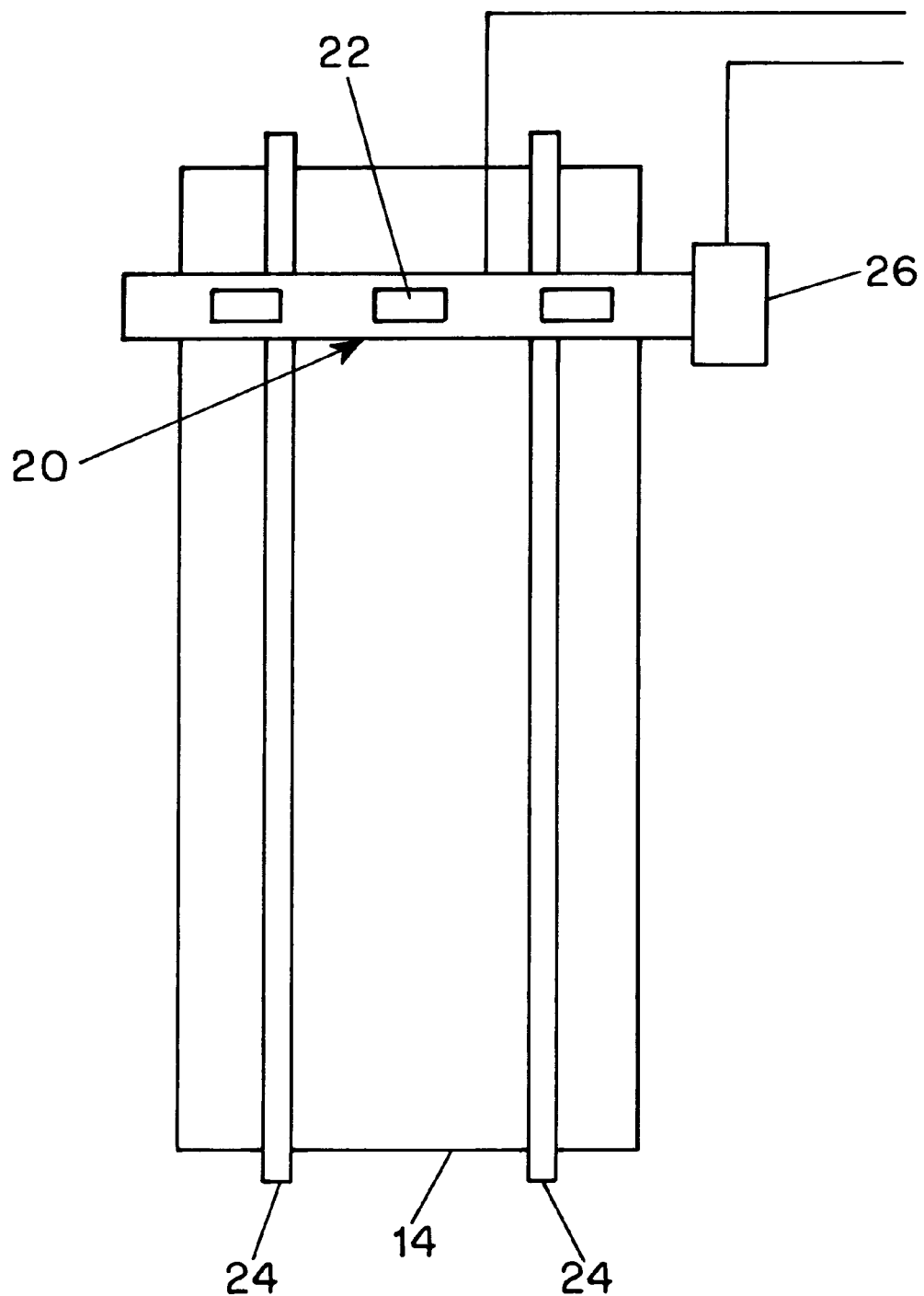
FIG. 2 is a plan view of portions of the FIG. 1 system.

FIG. 1 illustrates an embodiment of a microwave heating system, arranged to use controlled microwave energy to heat one or more body portions of a subject on a controlled basis, in accordance with the invention. For present purposes, a subject's blood is defined as a body portion. The FIG. 1 system includes a support unit 10, arranged to support the body of a human subject in a prone position. Support unit 10 may typically take the form a table-type structure of suitable dimensions of non-metallic or other appropriate construction. Support unit 10 may be arranged to directly support a sensor array 12 arranged to absorb all or a portion of incident microwave energy while providing a positional indication subject to interpretation as to the level of microwave energy incident upon discrete areas of the array. Sensor array 12 may comprise sections of energy absorptive material with associated thermocouple or other temperature sensing elements arrange to sense power levels on the basis of temperature rise, or other appropriate sensor devices. A suitable form of mattress or other body support element 14 is also provided to meet stability, comfort, sanitary and other direct body support considerations. Support element 14 is desirably of a construction substantially transparent to microwave energy. Straps or other body retention or restraint elements may also be provided.

The FIG. 1 system also includes a microwave power assembly 20, which is variably positionable relative to the support unit 10. The word "microwave" is nominally defined with reference to wavelengths from one to one hundred centimeters. Microwave power assembly 20 typically includes a transverse linear array of magnetron or other suitable microwave power supply devices 22 with appropriate local control circuitry, a single such device arranged for controlled scanning transversely across the surface of support element 14, or a combination thereof. As illustrated, the power assembly 20 is supported via longitudinal structural members 24 and includes a position adjustment element, shown as motor unit 26. Structural members 24 may be elongated steel rails held up by supports (not shown) extending from the ceiling, floor or support unit 10. The motor unit 26 is arranged to move the power assembly along members 22 to preselected positions or continuously or incrementally in a controlled manner.

As illustrated, the FIG. 1 system further includes a central processor unit (CPU) 30 coupled to the microwave power assembly 20. As shown, associated with CPU 30 are memory unit 32, keyboard unit 34 and display unit 36, together with such additional computer components and programming as may suitably be provided by skilled persons. CPU 30 is arranged to control at least one of (a) the power level of the microwave frequency radiated energy, (b) the focus of the beam or beams of microwave frequency radiated energy and (c) the direction of radiation of the beam of microwave frequency energy provided by microwave power assembly 20. In other embodiments, the frequency or one or more additional characteristics of the microwave frequency energy may also be controlled.

In application of the invention it will generally be desirable to carry out experimental tests to determine the power and duration of local application of microwave energy for a particular purpose. Thus, it is known that strains of viruses can be killed if the medium in which they exist is heated to a particular temperature. It is also know that microwave energy (e.g., as applied in a microwave oven) is usable to heat a medium having a water content to any desired temperature up to some maximum temperature. In application of the present invention, in a presently preferred implementation either a narrow fan beam of radiated microwave frequency energy or a laterally scanned spot type beam is caused to irradiate a narrow transverse section of a subject's body. The beam is then caused to move in controlled fashion longitudinally down the length of the subject's body. On the basis of energy input requirements experimentally predetermined for given body weight, or sensing of energy absorption and body temperature, narrow transverse incremental sections of the subject's body are sequentially heated to a temperature adequate for a purpose such as killing viruses in a continuous sequential process of one or more complete longitudinal scans enabling cooling to take place promptly after desired heating is achieved, so as to minimize permanent or temporary bodily injury. It will be appreciated, however, that in treatment of a fatal condition, some level of localized bodily damage or injury may be acceptable to the subject involved, in view of overall results which may be achievable.

With an understanding of the invention, persons skilled in relevant fields will be able to implement systems using the invention in a variety of forms. For example, techniques for the production, control and focusing of microwave energy pursuant to computer programming are well established in applications as diverse as microwave ovens and magnetron usage in radar applications. Also, scanning, monitoring, control and interpretation of results achieved are well established in various types of medical scanning and interpretation systems already in wide usage.

In certain implementations the microwave power assembly may include at least one magnetron type device positioned in one or more of the following locations relative to the support unit: above the support unit, below a body portion support surface of the support unit, to the left of the support unit, and to the right of the support unit, in order to heat all or substantial portions of the body of a subject. Alternatively, in killing tumorous cells or other localized matter, a single focused beam may need to be moved only a small distance in order to achieve a desired result. It will also be appreciated that in other embodiments in implementation of the invention the position adjustment element, shown above as motor unit 26, may be arranged to move the support unit 10 (or portions thereof) in order to controllably relatively position the microwave power assembly 20 and the support unit 10 longitudinally.

While there have been described the currently preferred embodiments of the invention, those skilled in the art will recognize that other and further modifications may be made without departing from the invention and it is intended to claim all modifications and variations as fall within the scope of the invention.

What is claimed is:

1. A system, to heat body portions using controlled microwave energy, comprising:

a support unit arranged to support a subject body portion;

a microwave power assembly comprising a plurality of microwave power supply devices, each of said microwave power supply devices being capable of irradiating a focused directional beam of microwave frequency energy at a controllable power level, said assembly being variably positionable relative to said support unit;

a position adjustment element arranged to electromechanically position said microwave power assembly; and a central processor unit coupled to said position adjustment element, arranged to control positioning of said microwave power assembly and arranged to control at least one of the power level, the beam focus and the beam direction of each of said beams of microwave frequency energy irradiated by said microwave power supply devices.

2. A system as in claim 1, wherein said support unit is a table structure suitable for support of a human subject.

3. The system of claim 2, wherein said position adjustment element is arranged to electromechanically position said microwave power assembly at any location along the entire length of a human subject.

4. A system as in claim 1, wherein said microwave power supply devices are magnetron devices.

5. A system as in claim 1, wherein at least one of said microwave power supply devices is positioned in at least one of the locations relative to said support unit, above the support unit, below a body portion support surface of said support unit, to the left of said support unit, and to the right of said support unit.

6. A system as in claim 1, wherein said position adjustment element comprises an electric motor arranged to electromechanically position said microwave power assembly along at least one structural rail extending longitudinally.

7. A system as in claim 1, wherein said central processor unit comprises a computer system with associated memory.

8. A system as in claim 1, additionally comprising radiation sensing means responsive to the power level of said radiated beams of microwave frequency energy.

9. The system of claim 1, wherein said microwave power assembly includes at least one of said microwave power supply devices positioned in at least one of the locations relative to said support unit to the left of said support unit and to the right of said support unit.

10. The system of claim 1, wherein the subject body portion is a head.

11. The system of claim 1, wherein said microwave power assembly comprises at least three of said microwave power supply devices, at least one of said devices positioned in at least one of the locations relative to the support unit to the left of said support unit and to the right of said support unit.

12. The system of claim 1, wherein at least one of said focused directional beams of microwave frequency energy is capable of being laterally scanned.

13. A method, to heat body portions using controlled microwave energy, comprising the steps of:

(a) positioning a subject body portion on a support unit;

(b) irradiating towards said subject body portion a plurality of focused directional beams of microwave frequency energy, each at a controllable power level, using a variably positionable microwave power assembly comprising a plurality of microwave power supply devices each being capable of irradiating a focused directional beam of microwave frequency energy at a controllable power level;

(c) electromechanically positioning said microwave power assembly relative to said support unit; and (d) controlling at least one of the power level, the beam focus and the beam direction of said beams of microwave frequency energy irradiated by said microwave power supply devices.

14. A method as in claim 13, wherein said step (c) positioning is coordinated with said step (d) controlling in order to provide a predetermined level of heating of said subject body portion.

15. A method as in claim 13, wherein step (c) comprises electromechanically moving said microwave power assembly a predetermined longitudinal distance at a predetermined rate.

* * * * *